United States Patent [19]

Taguchi et al.

[11] Patent Number: 4,912,135

[45] Date of Patent: Mar. 27, 1990

[54] AMIDE COMPOUNDS

[75] Inventors: Hiroaki Taguchi, Ibaraki, Japan; Takeo Katsushima, Nashville, Tenn.; Masakazu Ban, Mukoh; Akihiko Watanabe, Otsu, both of Japan

[73] Assignee: Toyo Boseki Kabushiki Kaisha, Osaka, Japan

[21] Appl. No.: 263,345

[22] Filed: Oct. 27, 1988

[30] Foreign Application Priority Data

Oct. 31, 1987 [JP] Japan .................. 62-276946

[51] Int. Cl.$^4$ ............... A61K 31/24; A61K 31/275; C07C 103/24; C07C 121/52
[52] U.S. Cl. .................. 514/522; 514/535; 514/563; 514/616; 514/533; 558/414; 558/416; 560/45; 560/251; 562/455; 564/153; 564/158
[58] Field of Search .......... 558/414, 416; 514/522, 514/533, 535, 563, 616; 560/45, 251; 562/455; 564/153, 158

[56] References Cited

U.S. PATENT DOCUMENTS

| | | | |
|---|---|---|---|
| 3,557,211 | 1/1971 | Rumanowski | 558/414 |
| 4,248,961 | 2/1981 | Hagen et al. | 564/158 |
| 4,250,113 | 2/1981 | Nordal et al. | 564/153 |
| 4,568,752 | 2/1986 | Fryberg | 564/153 |

*Primary Examiner*—Joseph Paul Brust
*Assistant Examiner*—Mary Sue Howard
*Attorney, Agent, or Firm*—Wegner & Bretschneider

[57] ABSTRACT

Novel amide compounds of the formula:

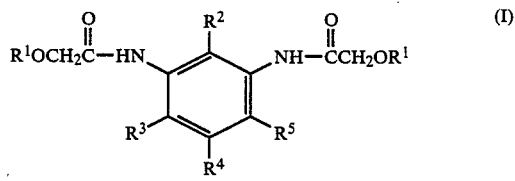

wherein $R^1$ is hydrogen, lower alkyl, acetyl, or propionyl; $R^2$ is hydrogen or chlorine; $R^3$ is hydrogen or a group of the formula: $-CO_2R^6$ (wherein $R^6$ is hydrogen, lower alkyl or alkali metal); $R^4$ is hydrogen, trifluoromethyl, cyano, aminocarbonyl, or a group of the formula: $-CO_2R^7$ (wherein $R^7$ is hydrogen, lower alkyl, or alkali metal); $R^5$ is hydrogen, or a group of the formula: $-CO_2R^8$ (wherein $R^8$ is hydrogen, lower alkyl, or alkali metal), which have excellent anti-allergic activity and are useful for the prophylaxis and treatment of various allergic diseases, and a pharmaceutical composition containing the amide compound as set forth above as an active ingredient.

8 Claims, No Drawings

AMIDE COMPOUNDS

This invention relates to novel amide compounds having an anti-allergic activity and being useful as an anti-allergic agent. More particularly, it relates to amide compounds of the formula:

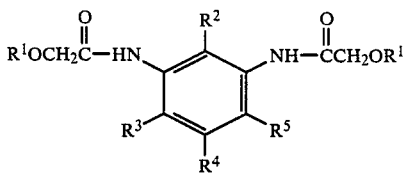

wherein $R^1$ is hydrogen atom, a lower alkyl group, acetyl group, or propionyl group; $R^2$ is hydrogen atom or chlorine atom; $R^3$ is hydrogen atom or a group of the formula: —$CO_2R^6$ (wherein $R^6$ is hydrogen atom, a lower alkyl group or an alkali metal); $R^4$ is hydrogen atom, trifluoromethyl group, cyano group, aminocarbonyl group, or a group of the formula: —$CO_2R^7$ (wherein $R^7$ is hydrogen atom, a lower alkyl group, or an alkali metal); $R^5$ is hydrogen atom, or a group of the formula: —$CO_2R^8$ (wherein $R^8$ is hydrogen atom, a lower alkyl group, or an alkali metal).

Prior Art

There have hitherto been studied various compounds useful for prophylaxis and treatment of various kinds of allergic symptoms. Known amide compounds having an anti-allergic acitivity are, for example, Tranilast [i.e. N-(3,4-dimethoxycinnamoyl)anthranilic acid] (cf. The Journal of Allergy and Clinical Immunology, Vol. 57, No. 5, page 396, 1976) and Lodoxamide Ethyl [i.e. diethyl N,N'-(2-chloro-5-cyano-m-phenylene)dioxamate] (cf. Agents and Actions, Vol. 1, page 235, 1979). However, known anti-allergic agents are not necessarily satisfactory for the treatment of various kinds of allergic diseases, particularly the treatment of bronchial asthma.

BRIEF DESCRIPTION OF THE INVENTION

The present inventors have intensively studied many kinds of compounds and the pharmacological activities thereof in order to find a compound having excellent anti-allergic activity and have found that some specific amide compounds can show excellent anti-allergic activity.

An object of the invention is to provide novel amide compounds having excellent anti-allergic activity against various kinds of allergic diseases. Another object of the invention is to provide a pharmaceutical composition containing said amide compounds as an active ingredient which is useful for the prophylaxis and treatment of various allergic diseases. Another object of the invention is to provide a process for preparating the amide compounds and pharmaceutical composition thereof. These and other objects and advantages of the invention will be apparent to those skilled in the art from the following description.

DETAILED DESCRIPTION OF THE INVENTION

The amide compounds of this invention are the compounds of the formula (I) as set forth hereinbefore.

In the formula (I), the lower alkyl group for $R^1$ includes alkyl groups having 1 to 6 carbon atoms, preferably methyl or ethyl group. The lower alkyl group for $R^6$, $R^7$ and $R^8$ include alkyl groups having 1 to 6 carbon atoms, preferably methyl or ethyl group, and the alkali metal includes sodium and potassium metal.

Preferred compounds of this invention are the amide compounds of the formula (I) wherein $R^1$ is hydrogen atom, an alkyl group having 1 to 6 carbon atoms, acetyl group or propionyl group; $R^2$ is hydrogen atom or chlorine atom; $R^3$ is hydrogen atom; $R^4$ is trifluoromethyl group, cyano group, aminocarbonyl group, or a group of the formula: —$CO_2R^7$ (wherein $R^7$ is hydrogen atom, an alkyl group having 1 to 6 carbon atoms, or an alkali metal); and $R^5$ is hydrogen atom.

More preferred compounds are the amide compounds of the formula (I) wherein $R^1$ is hydrogen atom, methyl, ethyl, acetyl, or propionyl; $R^2$ is hydrogen atom or chlorine atom; $R^3$ is hydrogen atom; $R^4$ is trifluoromethyl, cyano, aminocarbonyl, or a group of the formula: —$CO_2R^7$ (wherein $R^7$ is hydrogen atom, methyl, ethyl, sodium atom or potassium atom); and $R^5$ is hydrogen atom.

Specifically preferred compounds are the following compounds:
3,5-Bis(acetoxyacetylamino)-4-chlorobenzonitrile
3,5-Bis(hydroxyacetylamino)-4-chlorobenzonitrile
3,5-Bis(methoxyacetylamino)-4-chlorobenzonitrile
3,5-Bis(methoxyacetylamino)benzonitrile.

The amide compounds (I) of this invention can be prepared, for example, by the following process, which comprises reacting a diamino compound of the formula:

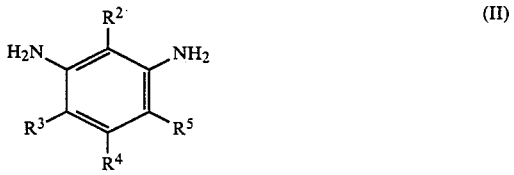

wherein $R^2$ is hydrogen atom or chlorine atom; $R^3$ is hydrogen atom or a group of the formula: —$CO_2R^6$ (wherein $R^6$ is hydrogen atom or a lower alkyl group); $R^4$ is hydrogen atom, trifluoromethyl group, cyano group, aminocarbonyl group, or a group of the formula: —$CO_2R^7$ (wherein $R^7$ is hydrogen atom or a lower alkyl group); $R^5$ is hydrogen atom, or a group of the formula: —$CO_2R^8$ (wherein $R^8$ is hydrogen atom or a lower alkyl group), with an acid halide of the formula:

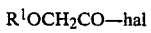

wherein $R^1$ is a lower alkyl group, acetyl group, propionyl group, or an alkoxyalkyl group, and hal is a halogen atom (e.g. chlorine atom).

The above reaction can be carried out in an aprotic solvent (e.g. pyridine, chloroform, etc.) in the presence of a base (e.g. pyridine, triethylamine, etc.). The reaction proceeds without heating, but may be carried out with heating in order to complete the reaction. In case of the compounds of the formula (I) wherein $R^1$ is acetyl or propionyl group, the obtained compounds may optionally be hydrolyzed to obtain the compounds of the formula (I) wherein $R^1$ is hydrogen atom.

When there are obtained the compounds of the formula (I) wherein one or more groups of $R^6$, $R^7$ and $R^8$ are hydrogen atom by the above reaction, the hydrogen atom may optionally be converted into an alkali metal by a usual method to give the compounds of the formula (I) wherein one or more groups of $R^6$, $R^7$ and $R^8$ are an alkali metal.

The compounds of the formula (I) wherein one or more groups of $R^6$, $R^7$ and $R^8$ are a lower alkyl group may be subjected to an ester exchange reaction, by which there can be prepared the compounds of the formula (I) wherein the corresponding one or more groups of $R^6$, $R^7$ and $R^8$ are an alkyl group different from the orignal alkyl group.

The compounds of this invention have potent inhibitory activity against immediate allergic reaction and hence are useful for the prophylaxis and treatment of immediate allergy, such as bronchial asthma, urticaria, allergic rhinitis, etc.

The anti-allergic activity of the compounds of this invention is illustrated by the following experiment.

Experiment

Male Wistar rats (weighing about 200 g) were passively sensitized by intradermal injection of each 0.1 ml of a solution of rat antiserum to egg albumin in each two sites (totally four sites) at both sides of dorsal median line. After 48 hours, each rat was challenged by injecting a mixture (1 ml) of egg albumin and Evans blue solution via tail vein to induce passive cutaneous anaphylaxis (PCA). 30 minutes after the challenge, the rats were sacrificed to take the blueing region, and the amount of pigment from the blueing region was measured by the method of Katayama et al. (cf. Microbiol. Immunol., Vol. 22, page 89, 1978). Test compounds were orally administered to the rats (each 6 rats) in a dose of 30 mg/kg 30 minutes before the antigen challenge. The PCA inhibitory rate of the compounds of this invention is shown in Table 1.

TABLE 1

| Test compounds | PCA inhibitory rate (%) |
|---|---|
| 1,3-Bis(methoxyacetylamino)benzene (compound in Example 1) | 24.9 |
| 3,5-Bis(methoxyacetylamino)-4-chloro-benzonitrile (compound in Example 2) | 90.6 |
| 3,5-Bis(methoxyacetylamino)benzoic acid (compound in Example 3) | 28.8 |
| 3,5-Bis(methoxyacetylamino)-4-chloro-benzamide.½ hydrate (compound in Example 5) | 26.9 |
| 3,5-Bis(ethoxyacetylamino)-4-chloro-benzonitrile (compound in Example 6) | 37.7 |
| 3,5-Bis(acetoxyacetylamino)-4-chloro-benzonitrile (compound in Example 7) | 93.4 |
| 3,5-Bis(hydroxyacetylamino)-4-chloro-benzonitrile (compound in Example 8) | 77.0 |
| 3,5-Bis(methoxyacetylamino)benzonitrile (compound in Example 13) | 88.1 |

The compounds of this invention can be administered by oral or parenteral route, preferably by oral route. Alternatively, the compounds may be administered by inhalation in the form of aerosol spray or with an inhalator in the form of dry powder so that the compound can contact directly with the lung.

The clinical dose of the compounds of this invention may vary according to the kinds of the compounds, administration routes, severity of diseases, age, sex and body weight of patients, or the like, but is usually in the range of 2 to 2,000 mg per day in the human. The dose may be divided and aministered in two to several times per day.

The compounds of this invention are usually administered to patients in the form of a pharmaceutical composition which contains a non-toxic and effective amount of the compounds. The pharmaceutical composition is in the dosage form of tablets, capsules, granules, syrups, powders, and the like for oral administration, and for the parenteral administration, they are in the form of aqueous solutions for intravenous injection, or oil suspension for intramuscular injection. The pharmaceutical composition is usually prepared by admixing the active compound (I) with conventional pharmaceutical carriers or diluents. Suitable examples of the carriers and diluents are lactose, glucose, dextrin, starch, sucrose, microcrystalline cellulose, sodium carboxymethylcellulose, calcium carboxymethylcellulose, gelatin, hydroxypropylcellulose, polyvinylpyrrolidone, magnesium stearate, talc, carboxyvinyl polymer, sorbitan fatty acid esters, sodium lauryl sulfate, macrogol, vegetable oils, wax, liquid paraffin, white petrolatum, propylene glycol, water, or the like.

This invention is illustrated by the following Examples but should not be construed to be limited thereto.

EXAMPLE 1

Preparation of 1,3-bis(methoxyacetylamino)benzene:

To a solution of m-phenylenediamine (5.41 g) in pyridine (100 ml) is added dropwise methoxyacetyl chloride (10 ml). The mixture is stirred at room temperature for 2 hours, and thereafter, pyridine is distilled off under reduced pressure. To the residue is added water, and the mixture is extracted with chloroform. The organic layer is dried over anhydrous sodium sulfate and distilled under reduced pressure to remove the solvent. The resulting crude crystals are recrystallized from ethyl acetate-hexane to give the title compound (9.89 g) having the following physical properties.

Melting point: 110°–111° C.

IR (KBr) $\nu$: 3300, 1665, 1600, 1535, 1445, 1205, 1120, 985, 775, 720, 525 cm$^{-1}$

NMR (CDCl$_3$) $\delta$: 8.25 (2H, br. s), 7.85 (1H, br. s), 7.30 (3H, m), 3.98 (4H, s), 3.48 (6H, s)

Elementary analysis: Calcd. (%) C,57.13; H,6.39; N,11.10; Found (%): C,57.42; H,6.37; N,11.06.

EXAMPLE 2

Preparation of 3,5-bis(methoxyacetylamino)-4-chlorobenzonitrile:

To a solution of 4-chloro-3,5-diaminobenzonitrile (3.34 g) in pyridine (60 ml) is added dropwise methoxyacetyl chloride (4.0 ml) at room temperature. The mixture is stirred at room temperature for 2 hours, and thereafter, pyridine is distilled off under reduced pressure. To the residue is added water, and the resulting solid substance is separated by filtration and washed with water. The resulting crude crystals are recrystallized from ethanol to give the title compound (5.1 g) having the following physical properties.

Melting point: 173°–174° C.

IR (KBr) $\nu$: 3380, 3120, 2950, 2845, 2240, 1715, 1590, 1550, 1505, 1435, 1300, 1200, 1115, 1050, 985, 900, 880, 675, 635 cm$^{-1}$

NMR (DMSO-d$_6$)$\delta$: 9.50 (2H, br. s), 8.11 (2H, s), 4.07 (4H, s), 3.41 (6H, s)

Elementary analysis: Calcd. (%): C,50.09; H,4.53; N,13.48; Cl,11.37; Found (%): C,50.11; H,4.34; N,13.50; Cl,11.47.

EXAMPLE 3

Preparation of 3,5-bis(methoxyacetylamino)benzoic acid:

To a solution of 3,5-diaminobenzoic acid (6.1 g) in pyridine (80 ml) is added dropwise methoxyacetyl chloride (8.0 ml) at room temperature, and the mixture is stirred for 2 hours as it stands. From the reaction mixture, pyridine is distilled off under reduced pressure. To the residue is added 1N hydrochloric acid, and the resulting solid substance is separated by filtration and washed with water. The resulting crude crystals are recrystallized from ethanol to give the title compound (8.0 g) having the following physical properties.

Melting point: 227°–229° C. (decomp.)

IR (KBr) $\nu$: 3425, 3300, 3120, 3020, 2950, 2840, 2600, 1725, 1685, 1645, 1605, 1560, 1455, 1430, 1370, 1300, 1230, 1210, 1135, 1115, 995, 925, 875, 770, 690, 675 $cm^{-1}$

NMR (DMSO-$d_6$) $\delta$: 12.87 (1H, br. s), 9.92 (2H, br. s), 8.32–8.17 (1H), 8.04–7.90 (2H), 3.97 (4H, s), 3.35 (6H, s)

Elementary analysis: Calcd. (%): C,52.70; H,5.44; N,9.46; Found (%): C,52.82; H,5.45; N,9.60.

EXAMPLE 4

Preparation of ethyl 2,4-bis(methoxyacetylamino)benzoate:

To a solution of ethyl 2,4-diaminobenzoate (3.6 g) in pyridine (80 ml) is added dropwise methoxyacetyl chloride (4.0 ml) at room temperature. The mixture is stirred at room temperature for 3 hours, and thereafter, pyridine is distilled off under reduced pressure. To the residue are added water and chloroform. The organic layer is separated and washed with water and then with aqueous saturated sodium chloride solution, and dried over anhydrous sodium sulfate. The solvent is distilled off under reduced pressure, and the resulting oily substance is dissolved in ethyl acetate-hexane, and the solution is allowed to stand at $-30°$ C. for 6 hours. The precipitated crystals are separated by filtration to give the title compound (6.0 g) having the following physical properties.

Melting point: 90°–91° C.

IR (KBr) $\nu$: 3420, 3390, 3000, 2950, 2840, 1715, 1700, 1685, 1610, 1590, 1550, 1525, 1480, 1455, 1415, 1375, 1305, 1280, 1260, 1205, 1155, 1120, 1105, 1090, 1000, 880, 700 $cm^{-1}$

NMR (DMSO-$d_6$) $\delta$: 11.50 (1H, br. s), 10.12 (1H, br. s), 8.86 (1H, d), 7.91 (1H, d), 7.55 (1H, dd), 4.28 (2H, q), 4.00 (4H, s), 3.42 (3H, s), 3.34 (3H, s), 1.32 (3H, t)

Elementary analysis: Calcd. (%): C,55.55; H,6.22; N,8.64; Found (%): C,55.57; H,6.24; N,8.64.

EXAMPLE 5

Preparation of 3,5-bis(methoxyacetylamino)-4-chlorobenzamide.½hydrate:

To a solution of 4-chloro-3,5-diaminobenzamide (2.8 g) in pyridine (40 ml) is added dropwise methoxyacetyl chloride (3.0 ml) at room temperature. The mixture is stirred at room temperature for 3 hours, and thereafter, pyridine is distilled off under reduced pressure. To the residue is added water, and the resulting solid substance is separated by filtration and washed with water. The resulting crude crystals are recrystallized from ethanolethyl acetate-hexane to give the title compound (4.0 g) having the following physical properties.

Melting point: 208°–209° C.

IR (KBr) $\nu$: 3440, 3370, 3220, 2950, 1710, 1680, 1615, 1585, 1510, 1435, 1385, 1300, 1250, 1195, 1110, 1040, 985, 770, 660 $cm^{-1}$

NMR (DMSO-$d_6$) $\delta$: 9.43 (2H, br. s), 8.11 (2H, s), 7.98 (1H, br. s), 7.40 (1H, br. s), 4.06 (4H, s), 3.42 (6H, s)

Elementary analysis: Calcd. (%): C,46.09; H,5.06; N,12.40; Cl,10.47; Found (%): C,45.84; H,5.16; N,12.29; Cl,10.47.

EXAMPLE 6

Preparation of 3,5-bis(ethoxyacetylamino)-4-chlorobenzonitrile:

To a solution of 4-chloro-3,5-diaminobenzonitrile (3.3 g) in pyridine (80 ml) is added dropwise ethoxyacetyl chloride (4.8 ml) at room temperature. The mixture is stirred at room temperature for 3 hours, and thereafter, pyridine is distilled off under reduced pressure. To the residue is added water, and the resulting solid substance is separated by filtration and washed with water. The resulting crude crystals are recrystallized from ethanol to give the title compound (4.0 g) having the following physical properties.

Melting point: 152°–153° C.

IR (KBr) $\nu$: 3370, 3100, 2980, 2900, 2235, 1720, 1710, 1580, 1540, 1510, 1500, 1430, 1405, 1370, 1340, 1295, 1240, 110, 1040, 1025, 950, 885, 870, 720, 670, 625 $cm^{-1}$

NMR (DMSO-$d_6$) $\delta$: 9.45 (2H, br. s), 8.15 (2H, s), 4.10 (4H, s), 3.60 (4H, q), 1.21 (6H, t)

Elementary analysis: Calcd. (%): C,53.02; H,5.34; N,12.37; Cl,10.43; Found (%): C,53.15; H,5.33; N,12.51; Cl,10.43.

EXAMPLE 7

Preparation of 3,5-bis(acetoxyacetylamino)-4-chlorobenzonitrile:

To a solution of 4-chloro-3,5-diaminobenzonitrile (6.7 g) in pyridine (150 ml) is added dropwise acetoxyacetyl chloride (9.5 ml) at room temperature. The mixture is stirred at room temperature for 3 hours, and thereafter, pyridine is distilled off under reduced pressure. To the residue is added water, and the resulting solid substance is separated by filtration and dissolved in chloroform, and the insoluble substance is filtered off. The filtrate is washed with water and then with aqueous saturated sodium chloride solution, dried over anhydrous sodium sulfate, and then distilled under reduced pressure to remove the solvent. The resulting solid substance is recrystallized from ethanol to give the title compound (4.3 g) having the following physical properties.

Melting point: 193°–195° C.

IR (KBr) $\nu$: 3420, 3330, 2240, 1755, 1710, 1585, 1520, 1435, 1370, 1270, 1250, 1230, 1195, 1090, 1055, 870 $cm^{-1}$

NMR (DMSO-$d_6$) $\delta$: 9.94 (2H, br. s), 7.95 (2H, s), 4.73 (4H, s), 2.10 (6H, s)

Elementary analysis: Calcd. (%): C,48.99; H,3.84; N,11.43; Cl,9.64; Found (%): C,49.05; H,3.92; N,11.49; Cl,9.50.

EXAMPLE 8

Preparation of 3,5-bis(hydroxyacetylamino)-4-chlorobenzonitrile:

3,5-Bis(acetoxyacetylamino)-4-chlorobenzonitrile (2.7 g) prepared in Example 7 is suspended in 15% ammomiamethanol solution (80 ml), and the mixture is refluxed for 4 hours. After the reaction mixture is allowed to cool, the resulting crude crystals are separated by filtration and recrystallized from ethanol to give the title compound (1.3 g) having the following physical properties.

Melting point: decomposed from 228° C.

IR (KBr) ν: 3380, 3340, 3125, 2920, 2245, 1680, 1580, 1515, 1510, 1435, 1420, 1325, 1300, 1245, 1220, 1090, 1080, 1055, 995, 885, 880, 720, 710, 635 cm$^{-1}$

NMR (DMSO-d$_6$) δ: 8.27 (2H, s), 7.85 (2H, br. s), 4.70 (4H, s), 3.30 (2H, br. s)

Elementary analysis: Calcd. (%): C,46.58; H,3.55; N,14.81; Cl,12.50; Found (%): C,46.57; H,3.73; N,14.81; Cl,12.24.

EXAMPLE 9

Preparation of methyl 3,5-bis(methoxyacetylamino)-4-chlorobenzoate:

To a solution of methyl 4-chloro-3,5-diaminobenzoate dihydrochloride (1.1 g) in pyridine (20 ml) is added dropwise methoxyacetyl chloride (0.8 ml) at room temperature. The mixture is stirred at room temperature for 1.5 hour, and thereafter, pyridine is distilled off under reduced pressure. To the residue is added water, and the resulting solid substance is separated by filtration and washed with water. The resulting crude crystals are recrystallized from ethanol to give the title compound (1.1 g) having the following physical properties.

Melting point: 162°–164° C.

IR (KBr) ν: 3440, 3410, 3150, 3040, 2980, 2920, 2860, 1730, 1710, 1605, 1555, 1525, 1510, 1455, 1355, 1315, 1270, 1250, 1200, 1120, 1020, 1000, 970, 915, 810, 785, 735, 675 cm$^{-1}$

NMR (DMSO-d$_6$) δ: 9.41 (2H, br. s), 8.28 (2H, s), 4.07 (4H, s), 3.85 (3H, s), 3.43 (6H, s)

Elementary analysis: Calcd. (%): C,48.78; H,4.97; N,8.13; Cl,10.28; Found (%): C,48.73; H,5.10; N,8.13; Cl,10.13.

EXAMPLE 10

Preparation of 3,5-bis(methoxyacetylamino)-4-chlorobenzotrifluoride:

To a solution of 4-chloro-3,5-diaminobenzotrifluoride (4.2 g) in pyridine (80 ml) is added dropwise methoxyacetyl chloride (4.0 ml) at room temperature. The mixture is stirred at room temperature for 3 hours, and thereafter, pyridine is distilled off under reduced pressure. To the residue is added water, and the resulting solid substance is separated by filtration and washed with water. The resulting crude crystals are recrystallized from ethanol to give the title compound (5.0 g) having the following physical properties.

Melting point: 160°–162° C.

IR (KBr) ν: 3380, 3130, 3020, 2960, 2840, 1715, 1605, 1550, 1510, 1500, 1445, 1365, 1300, 1270, 1250, 1195, 1170, 1120, 1050, 980, 920, 880, 730, 720, 660 cm$^{-1}$

NMR (DMSO-d$_6$) δ: 9.50 (2H, br. s), 8.08 (2H, s), 4,08 (4H, s), 3.41 (6H, s)

Elementary analysis: Calcd. (%): C,44.02; H,3.98; N,7.90; Cl,9.99; F,16.07; Found (%): C,44.17; H,3.97; N,7.95; Cl,9.87; F,15.99.

EXAMPLE 11

Preparation of methyl 3,5-bis(methoxyacetylamino)-benzoate:

To a solution of methyl 3,5-diaminobenzoate dihydrochloride (7.2 g) in pyridine (100 ml) is added dropwise methoxyacetyl chloride (6.0 ml) at room temperature. The mixture is stirred at room temperature for 2 hours, and thereafter, pyridine is distilled off under reduced pressure. To the residue is added water and chloroform. The organic layer is separated and washed with water and then with aqueous saturated sodium chloride solution, dired over anhydrous sodium sulfate, and distilled under reduced pressure to remove the solvent. The resulting solid substance is recrystallized from ethanol to give the title compound (5.2 g) having the following physical properties.

Melting point: 140°–141° C.

IR (KBr) ν: 3280, 2970, 2930, 2850, 1725, 1680, 1615, 1610, 1550, 1460, 1440, 1355, 1320, 1250, 1210, 1135, 1120, 1035, 1015, 990, 930, 885, 775 cm$^{-1}$

NMR (DMSO-d$_6$) δ: 9.92 (2H, br. s), 8.25 (1H, t), 7.99 (2H, d), 3.98 (4H, s), 3.82 (3H, s), 3.35 (6H, s)

Elementary analysis: Calcd. (%): C,54.19; H,5.85; N,9.03; Found (%): C,54.12; H,5.85; N,9.00.

EXAMPLE 12

Preparation of 4,6-bis(methoxyacetylamino)-m-phthalic acid:

To a solution of 4,6-diamino-m-phthalic acid (5.4 g) in pyridine (100 ml) is added dropwise methoxyacetyl chloride (5.5 ml) at room temperature. The mixture is stirred at room temperature overnight, and thereafter, pyridine is distilled off under reduced pressure. To the residue are added water and 2N hydrochloric acid. The resulting solid substance is separated by filtration and washed with water. The resulting crude crystals are recrystallized from ethanol-water to give the title compound (5.0 g) having the following physical properties.

Melting point: 277°–281° C. (decomp.)

IR (KBr) ν: 3460, 3270, 2950, 1720, 1660, 1585, 1530, 1460, 1420, 1345, 1315, 1255, 1115, 985, 810, 680 cm$^{-1}$

NMR (DMSO-d$_6$) δ: 12.00 (2H, s), 9.94 (1H, s), 8.63 (1H, s), 4.03 (4H, s), 3.42 (6H, s)

Elementary analysis: Calcd. (%): C,49.41; H,4.74; N,8.23; Found (%): C,49.23; H,4.80; N,8.07.

EXAMPLE 13

Preparation of 3,5-bis(methoxyacetylamino)benzonitrile:

To a solution of 3,5-diaminobenzonitrile monohydrochloride (5.1 g) in pyridine (100 ml) is added dropwise methoxyacetyl chloride (6.0 ml) at room temperature. The mixture is stirred at room temperature for 2 hours, and thereafter, pyridine is distilled off under reduced pressure. To the residue is added water and the mixture is extracted with ethyl acetate. The organic layer is washed with water and then with aqueous saturated sodium chloride solution and dried over anhydrous sodium sulfate. After distilling off the solvent, the resulting solid substance is recrystallized from ethyl acetate-n-hexane to give the title compound (3.2 g) having the following physical properties.

Melting point: start to melt at 144.0° C. while decomposing

IR (KBr) ν: 3290, 2950, 2230, 1675, 1600, 1550, 1530, 1445, 1425, 1345, 1280, 1255, 1200, 1105, 985, 915, 865, 715 cm$^{-1}$

NMR (DMSO-d$_6$) δ: 10.04 (2H, br. s), 8.28 (1H, t), 7.74 (2H, d), 4.00 (4H, s), 3.84 (6H, s)

Elementary analysis: Calcd. (%): C,56.31; H,5.45; N,15.15; Found (%): C,56.30; H,5.52; N,15.24.

EXAMPLE 14

Preparation of 3,5-bis(propionyloxyacetylamino)-4-chlorobenzonitrile:

To a suspension of 4-chloro-3,5-diaminobenzonitrile (1.67 g) in chloroform (80 ml) is added triethylamine (2.77 ml) and thereto is added dropwise propionyloxyacetyl chloride (3.0 g) under cooling on ice bath. The mixture is stirred at room temperature for 6 hours, and thereto is further added dropwise propionyloxyacetyl chloride (0.8 g) under cooling on ice bath. The mixture is stirred at room temperature for 2 hours, and thereto is added triethylamine (0.73 ml). To the mixture is further added dropwise propionyloxyacetyl chloride (0.8 g) under cooling on ice bath. After stirring the mixture at room temperature for 3 hours, diethyl ether (40 ml) is added to the mixture. The resulting solid substance is separated by filtration and washed with a mixture of chloroform-diethyl ether (1:1) and then with water, and is recrystallized from ethanol to give the title compound (1.2 g) having the following physical properties.

Melting point: gradually decomposed from 141° C.

IR (KBr) $\nu$: 3410, 3270, 2230, 1760, 1690, 1580, 1530, 1430, 1170, 890, 850, 810 cm$^{-1}$

NMR (DMSO-d$_6$) $\delta$: 9.93 (2H, br. s), 7.97 (2H, s), 4.75 (4H, s), 2.43 (4H, q), 1.09 (6H, t)

Elementary analysis: Calcd. (%): C,51.59; H,4.58; N,10.62; Cl,8.96; Found (%): C,51.62; H,4.64; N,10.53; Cl,8.82.

What is claimed is:

1. An amide compound of the formula:

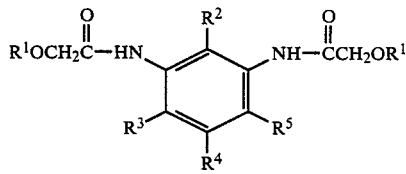

wherein $R^1$ is hydrogen atom, a lower alkyl group, acetyl group, or propionyl group; $R^2$ is hydrogen atom or chlorine atom; $R^3$ is hydrogen atom or a group of the formula: $-CO_2R^6$ (wherein $R^6$ is hydrogen atom, a lower alkyl group or an alkali metal); $R^4$ is hydrogen atom, trifluoromethyl group, cyano group, aminocarbonyl group, or a group of the formula: $-CO_2R^7$ (wherein $R^7$ is hydrogen atom, a lower alkyl group, or an alkali metal); $R^5$ is hydrogen atom, or a group of the formula $-CO_2R^8$ (wherein $R^8$ is hydrogen atom, a lower alkyl group, or an alkali metal).

2. The compound according to claim 1, wherein $R^1$ is hydrogen atom, an alkyl group having 1 to 6 carbon atoms, acetyl group or propionyl group; $R^2$ is hydrogen atom or chlorine atom; $R^3$ is hydrogen atom; $R^4$ is trifluoromethyl group, cyano group, aminocarbonyl group, or a group of the formula: $-CO_2R^7$ (wherein $R^7$ is hydrogen atom, an alkyl group having 1 to 6 carbon atoms, or an alkali metal); and $R^5$ is hydrogen atom.

3. The compound according to claim 1, wherein $R^1$ is hydrogen atom, methyl, ethyl, acetyl, or propionyl; $R^2$ is hydrogen atom or chlorine atom; $R^3$ is hydrogen atom; $R^4$ is trifluoromethyl, cyano, aminocarbonyl, or a group of the formula $-CO_2R^7$ (wherein $R^7$ is hydrogen atom, methyl, ethyl, sodium atom or potassium atom); and $R^5$ is hydrogen atom.

4. A pharmaceutical composition for the prophylaxis and treatment of allergic diseases, which comprises as an active ingredient a pharmaceutically effective amount of an amide compound as set forth in claim 1 in admixture with a pharmaceutical carrier or diluent.

5. The compound 3,5-bis(acetoxyacetylamino)-4-chlorobenzonitrile in accordance with claim 1.

6. The compound 3,5-bis(hydroxyacetylamino)-4-chlorobenzonitrile in accordance with claim 1.

7. The compound 3,5-bis(methoxyacetylamino)-4-chlorobenzonitrile in accordance with claim 1.

8. The compound 3,5-bis(methoxyacetylamino)benzonitrile in accordance with claim 1.

* * * * *